United States Patent
Okuyama et al.

(10) Patent No.: US 10,538,477 B2
(45) Date of Patent: Jan. 21, 2020

(54) PRODUCTION INTERMEDIATE OF POLYMERIZABLE COMPOUND, PRODUCTION METHOD FOR SAME, COMPOSITION, AND STABILIZATION METHOD

(71) Applicant: ZEON CORPORATION, Chiyoda-ku, Tokyo (JP)

(72) Inventors: Kumi Okuyama, Tokyo (JP); Kei Sakamoto, Tokyo (JP); Kanako Sanuki, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 15/320,512

(22) PCT Filed: Jun. 30, 2015

(86) PCT No.: PCT/JP2015/068912
§ 371 (c)(1),
(2) Date: Dec. 20, 2016

(87) PCT Pub. No.: WO2016/002816
PCT Pub. Date: Jan. 7, 2016

(65) Prior Publication Data
US 2017/0158604 A1 Jun. 8, 2017

(30) Foreign Application Priority Data
Jun. 30, 2014 (JP) .................................. 2014-134770

(51) Int. Cl.
*C07C 67/62* (2006.01)
*C07C 67/307* (2006.01)
*C07C 69/75* (2006.01)
*C07C 69/017* (2006.01)

(52) U.S. Cl.
CPC ............ *C07C 67/62* (2013.01); *C07C 67/307* (2013.01); *C07C 69/017* (2013.01); *C07C 69/75* (2013.01); *C07C 2101/14* (2013.01)

(58) Field of Classification Search
CPC ... C07C 2601/14; C07C 67/307; C07C 67/62; C07C 69/017; C07C 69/75; C07C 2101/14
See application file for complete search history.

(56) References Cited

U.S. PATENT DOCUMENTS

| | | | | |
|---|---|---|---|---|
| 5,567,349 A | * | 10/1996 | Kelly | ...................... C07C 69/92 252/299.01 |
| 5,780,629 A | * | 7/1998 | Etzbach | .................. C07C 69/92 252/299.01 |
| 6,335,462 B1 | | 1/2002 | Etzbach et al. | |
| 2015/0175564 A1 | | 6/2015 | Sakamoto et al. | |
| 2017/0015639 A1 | | 1/2017 | Okuyama et al. | |

FOREIGN PATENT DOCUMENTS

| | | |
|---|---|---|
| CN | 1110984 A | 11/1995 |
| CN | 1141645 A | 1/1997 |
| CN | 1245484 A | 2/2000 |
| CN | 106068257 A | 11/2016 |
| EP | 0739403 A1 | 10/1996 |
| JP | S646008 A | 1/1989 |
| JP | H0348639 A | 3/1991 |
| JP | H07278060 A | 10/1995 |
| JP | H09506088 A | 6/1997 |
| JP | 2001505879 A | 5/2001 |
| JP | 2010083799 A | 4/2010 |
| JP | 2010270108 | 12/2010 |
| JP | 2012077056 | 4/2012 |
| JP | 2012077057 | 4/2012 |
| JP | 2012097078 | 5/2012 |
| JP | 2013-018714 * | 1/2013 |
| JP | 2013018714 A | 1/2013 |
| WO | 201401325 A1 | 1/2014 |

OTHER PUBLICATIONS

English Translation of JP2013-018714, Jan. 31, 2013, pp. 1-29.*
Jan. 3, 2017, International Preliminary Report on Patentability issued in the International Patent Application No. PCT/JP2015/068912.
Sep. 1, 2015, International Search Report issued in the International Patent Application No. PCT/JP2015/068912.
Jan. 3, 2018, Extended European Search Report issued by the European Patent Office in the corresponding European Patent Application No. 15814347.9.
Nov. 30, 2018, Communication pursuant to Atricle 94(3) EPC issued by the European Patent Office in the corresponding European Patent Application No. 15814347.9.

* cited by examiner

*Primary Examiner* — Yevgeny Valenrod
*Assistant Examiner* — Blaine G Doletski
(74) *Attorney, Agent, or Firm* — Kenja IP Law PC

(57) ABSTRACT

Provided are a production method for compound (II) including reacting compound (I) with a halogenating agent in the presence of at least 0.5 equivalents, relative to compound (I), of a nitrogen atom-containing polar aprotic solvent; a composition containing compound (II), a halogenating agent or the like, and at least 0.5 equivalents, relative to compound (II), of a nitrogen atom-containing polar aprotic solvent; a stabilization method for compound (II); and compound (II).

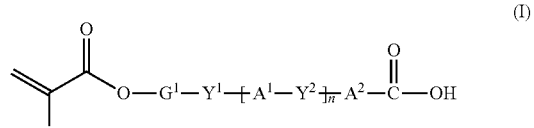

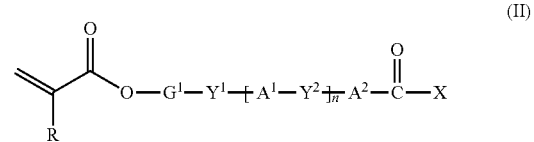

14 Claims, 1 Drawing Sheet

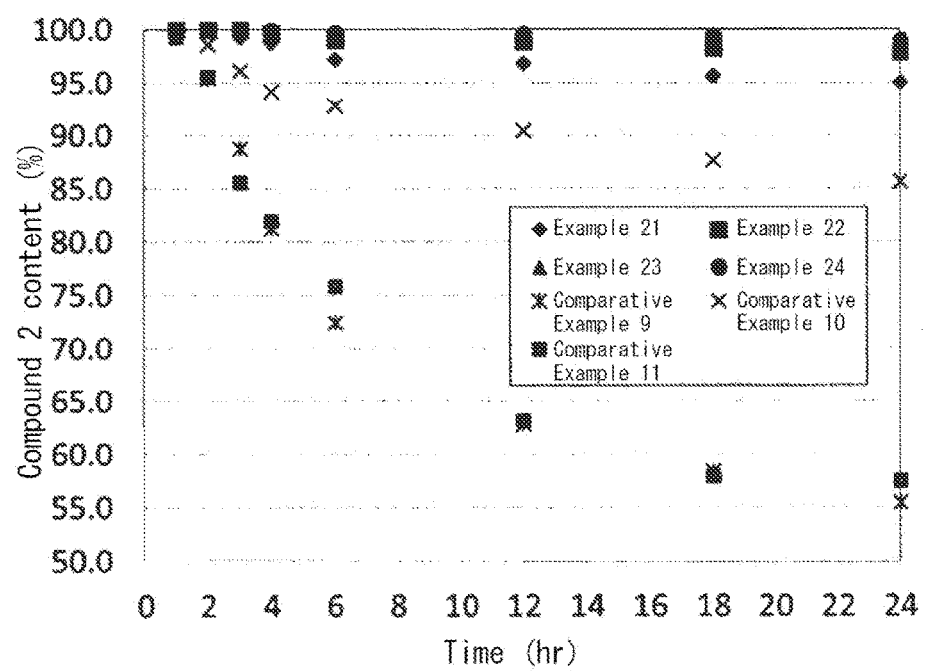

PRODUCTION INTERMEDIATE OF POLYMERIZABLE COMPOUND, PRODUCTION METHOD FOR SAME, COMPOSITION, AND STABILIZATION METHOD

TECHNICAL FIELD

The present disclosure relates to a production intermediate of a polymerizable compound that can be used in preparation of an optical film capable of uniform polarized light conversion over a wide wavelength range, a method for producing this production intermediate with a high purity in an industrially advantageous manner, a composition in which this production intermediate is stabilized by a nitrogen atom-containing polar aprotic solvent, and a stabilization method for this production intermediate.

A carboxylic acid halide having a (meth)acryloyl group is conventionally known as a compound that is useful, for example, as a production intermediate in production of a liquid-crystal material or an electron transport material through an esterification reaction with a compound having a phenolic hydroxy group.

The carboxylic acid halide having the (meth)acryloyl group can be obtained by a method in which a carboxylic acid having a (meth)acryloyl group is reacted with a halogenating agent.

However, at the stage at which the carboxylic acid having the (meth)acryloyl group is reacted with the halogenating agent in this method, in addition to the target carboxylic acid halide, a side reaction product (halogenated by-product) is also produced through halogen atom addition at a double bond of the (meth)acryloyl group, which is problematic as it reduces the purity of the target product.

In response to this problem, PTL 1 proposes a method in which, after an esterification reaction, an impurity (halogenated by-product) that has been produced is converted back to a (meth)acrylate in the presence of a base.

However, this method is complicated since it requires an additional step after the esterification reaction in order to convert the impurity back to the (meth)acrylate using the base.

Another problem is that during storage of a reaction mixture obtained by reacting a carboxylic acid having a (meth)acryloyl group with a halogenating agent, a carboxylic acid halide having a (meth)acryloyl group that is contained in the mixture is gradually converted to a halogenated by-product, leading to reduced purity of the carboxylic acid halide.

CITATION LIST

Patent Literature

PTL 1: JP 2010-83799 A

SUMMARY

Technical Problem

The present disclosure is made in light of the conventional techniques described above and an objective thereof is to provide a method for producing a carboxylic acid halide having a (meth)acryloyl group with a high purity and in an industrially advantageous manner, a composition in which this carboxylic acid halide is stabilized by a nitrogen atom-containing polar aprotic solvent, a stabilization method for this carboxylic acid halide, and the carboxylic acid halide.

Solution to Problem

The inventors conducted diligent investigation in order to solve the problems described above, resulting in the discovery that when a carboxylic acid compound having a (meth)acryloyl group is reacted with a halogenating agent, a halogen atom addition reaction at a double bond of the (meth)acryloyl group can be inhibited by providing a specific amount of a nitrogen atom-containing polar aprotic solvent in the reaction system, and, as a consequence, a target carboxylic acid halide can be obtain with a high purity and a high yield. Moreover, the inventors discovered that when a specific amount of a nitrogen atom-containing polar aprotic solvent is provided in an organic solvent solution containing the target carboxylic acid halide, conversion of the carboxylic acid halide to a halogenated by-product in the organic solvent solution can be inhibited even when the organic solvent solution is stored for a long time. These discoveries led to the present disclosure.

Accordingly, the present disclosure provides production methods for a polymerizable compound described in sections (1) to (7), compositions described in sections (8) to (11), a stabilization method described in section (12), and compounds described in sections (13) to (15).

(1) A production method for a compound represented by formula (II)

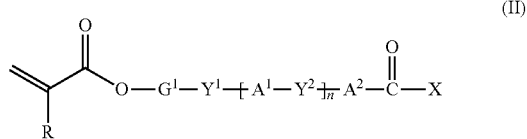

comprising
reacting a compound represented by formula (I)

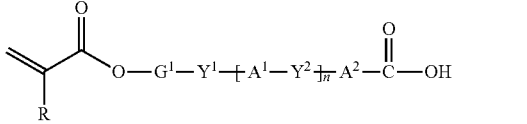

with a halogenating agent in the presence of at least 0.5 equivalents, relative to the compound represented by formula (I), of a nitrogen atom-containing polar aprotic solvent, wherein in formula (I):

R represents a hydrogen atom or a methyl group;

$Y^1$ and $Y^2$ each represent, independently of one another, a chemical single bond, —O—, —S—, —O—C(=O)—, —C(=O)—O—, —O—C(=O)—O—, —NR$^1$—C(=O)—, or —C(=O)—NR$^1$—, where R$^1$ represents a hydrogen atom or an alkyl group having a carbon number of 1-6;

$G^1$ represents an optionally substituted divalent chain aliphatic group having a carbon number of 1-20 that may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—, but is not interrupted by two or more adjacent —O— or —S—, where $R^2$ represents a hydrogen atom or an alkyl group having a carbon number of 1-6;

$A^1$ and $A^2$ each represent, independently of one another, an optionally substituted divalent aromatic hydrocarbon group having a carbon number of 3-12 or an optionally substituted divalent alicyclic hydrocarbon group having a carbon number of 3-12; and n represents 0 or 1, and in formula (II), R, $G^1$, $Y^1$, $Y^2$, $A^1$, $A^2$, and n represent the same as above, and X represents a halogen atom.

(2) The production method described in section (1), wherein the halogenating agent is a chlorinating agent or a brominating agent.

(3) The production method described in section (1) or (2), wherein the compound represented by formula (I) is a compound for which, in formula (I), $Y^1$ and $Y^2$ are each, independently of one another, a chemical single bond, —O—, —O—C(=O)—, or —C(=O)—O—, and $G^1$ is an optionally substituted divalent chain aliphatic group having a carbon number of 1-20.

(4) The production method described in any one of sections (1) to (3), wherein the compound represented by formula (I) is a compound for which, in formula (I), $A^1$ and $A^2$ are each, independently of one another, an optionally substituted phenylene group or an optionally substituted cyclohexylene group.

(5) The production method described in any one of sections (1) to (4), wherein the nitrogen atom-containing polar aprotic solvent is an amide solvent.

(6) The production method described in any one of sections (1) to (5), wherein the nitrogen atom-containing polar aprotic solvent is at least one selected from the group consisting of N,N-dimethylformamide, N,N-dimethylacetamide, N-methylpyrrolidone, and 1,3-dimethyl-2-imidazolidinone.

(7) The production method described in any one of sections (1) to (6), further comprising after the reacting, concentrating a reaction liquid and removing either or both of unreacted halogenating agent and a halogenating agent-derived product.

(8) A composition comprising:

a compound represented by formula (II);

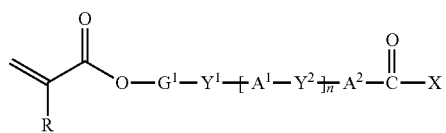

(II)

either or both of a halogenating agent and a halogenating agent-derived product; and a nitrogen atom-containing polar aprotic solvent in an amount of at least 0.5 equivalents relative to the compound represented by formula (II), wherein in formula (II):

R represents a hydrogen atom or a methyl group;

$Y^1$ and $Y^2$ each represent, independently of one another, a chemical single bond, —O—, —S—, —O—C(=O)—, —C(=O)—O—, —O—C(=O)—O—, —NR$^1$—C(=O)—, or —C(=O)—NR$^1$—, where $R^1$ represents a hydrogen atom or an alkyl group having a carbon number of 1-6;

$G^1$ represents an optionally substituted divalent chain aliphatic group having a carbon number of 1-20 that may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—, but is not interrupted by two or more adjacent —O— or —S—, where $R^2$ represents a hydrogen atom or an alkyl group having a carbon number of 1-6;

$A^1$ and $A^2$ each represent, independently of one another, an optionally substituted divalent aromatic hydrocarbon group having a carbon number of 3-12 or an optionally substituted divalent alicyclic hydrocarbon group having a carbon number of 3-12;

X represents a halogen atom; and n represents 0 or 1.

(9) The composition described in section (8), further comprising an organic solvent other than the nitrogen atom-containing polar aprotic solvent.

(10) The composition described in section (8) or (9), wherein the nitrogen atom-containing polar aprotic solvent is an amide solvent.

(11) The composition described in section (8) or (9), wherein the nitrogen atom-containing polar aprotic solvent is at least one selected from the group consisting of N,N-dimethylformamide, N,N-dimethylacetamide, N-methylpyrrolidone, and 1,3-dimethyl-2-imidazolidinone.

(12) A stabilization method for a compound represented by formula (II)

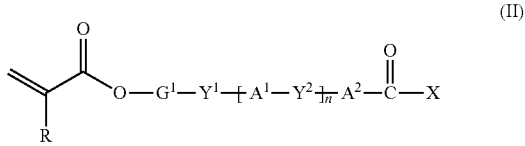

(II)

comprising providing a nitrogen atom-containing polar aprotic solvent, in an amount of at least 0.5 equivalents relative to the compound represented by formula (II), in an organic solvent solution containing the compound represented by formula (II) and either or both of a halogenating agent and a halogenating agent-derived product, wherein in formula (II):

R represents a hydrogen atom or a methyl group;

$Y^1$ and $Y^2$ each represent, independently of one another, a chemical single bond, —O—, —S—, —O—C(=O)—, —C(=O)—O—, —O—C(=O)—O—, —NR$^1$—C(=O)—, or —C(=O)—NR$^1$—, where $R^1$ represents a hydrogen atom or an alkyl group having a carbon number of 1-6;

$G^1$ represents an optionally substituted divalent chain aliphatic group having a carbon number of 1-20 that may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—, but is not interrupted by two or more adjacent —O— or —S—, where $R^2$ represents a hydrogen atom or an alkyl group having a carbon number of 1-6;

$A^1$ and $A^2$ each represent, independently of one another, an optionally substituted divalent aromatic hydrocarbon group having a carbon number of 3-12 or an optionally substituted divalent alicyclic hydrocarbon group having a carbon number of 3-12;

X represents a halogen atom; and n represents 0 or 1.

(13) A compound represented by formula (II)

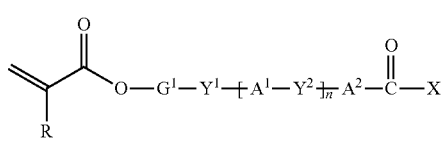

where, in formula (II):

R represents a hydrogen atom or a methyl group;

$Y^1$ and $Y^2$ each represent, independently of one another, a chemical single bond, —O—, —S—, —O—C(=O)—, —C(=O)—O—, —O—C(=O)—O—, —NR$^1$—C(=O)—, or —C(=O)—NR$^1$—, where $R^1$ represents a hydrogen atom or an alkyl group having a carbon number of 1-6;

$G^1$ represents an optionally substituted divalent chain aliphatic group having a carbon number of 1-20 that may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—, but is not interrupted by two or more adjacent —O— or —S—, where $R^2$ represents a hydrogen atom or an alkyl group having a carbon number of 1-6;

$A^1$ and $A^2$ each represent, independently of one another, an optionally substituted divalent aromatic hydrocarbon group having a carbon number of 3-12 or an optionally substituted divalent alicyclic hydrocarbon group having a carbon number of 3-12;

X represents a halogen atom; and n represents 0 or 1.

(14) The compound described in section (13), wherein in formula (II), n is 1.

(15) The compound described in section (13) or (14), wherein in formula (II), X is a fluorine atom, a chlorine atom, or a bromine atom.

Advantageous Effect

According to the presently disclosed production method, when the compound represented by formula (I) (carboxylic acid having a (meth)acryloyl group) is reacted with a halogenating agent to produce a corresponding carboxylic acid halide, the target carboxylic acid halide (compound represented by formula (II)) can be obtained with a high purity and a high yield without a halogen atom addition reaction occurring at a double bond of the (meth)acryloyl group.

As a result of the compound represented by formula (II) being obtained in a high purity, the compound represented by formula (II) can be suitably used as a production intermediate for a liquid-crystal material, an electron transport material, or the like.

The presently disclosed composition contains the compound represented by formula (II), either or both of a halogenating agent and a halogenating agent-derived product, and a specific amount of a nitrogen atom-containing polar aprotic solvent. In the presently disclosed composition, the compound represented by formula (II) is stabilized by the nitrogen atom-containing polar aprotic solvent. Consequently, conversion of the compound represented by formula (II) to a halogenated by-product (compound represented by formula (III) shown further below) by halogen atom addition at the double bond of the (meth)acryloyl group and a resulting decrease in the content of the compound represented by formula (II) in the composition do not occur even when the presently disclosed composition is stored for a long time.

BRIEF DESCRIPTION OF THE DRAWING

In the accompanying drawing

FIGURE is a graph illustrating change in content (%) of compound 2 over time.

DETAILED DESCRIPTION

The following provides a detailed description of the present disclosure that is divided into sections pertaining to 1) a production method for compound (II), 2) a composition, 3) a stabilization method for compound (II), and 4) compound (II).

1) Production Method for Compound (II)

The presently disclosed production method includes reacting a compound represented by formula (I) (hereinafter also referred to as compound (I))

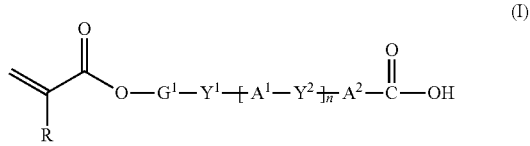

with a halogenating agent in the presence of at least 0.5 equivalents, relative to compound (I), of a nitrogen atom-containing polar aprotic solvent to produce a compound represented by formula (II) (hereinafter also referred to as compound (II)).

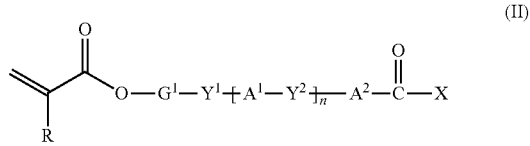

According to the presently disclosed production method, production of a halogenated by-product represented by formula (III) (hereinafter also referred to as compound (III))

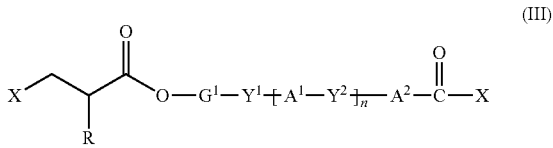

can be inhibited, and compound (II) can be obtained with a high purity and a high yield.

In formula (I), R represents a hydrogen atom or a methyl group.

$Y^1$ and $Y^2$ each represent, independently of one another, a chemical single bond, —O—, —S—, —O—C(=O)—, —C(=O)—O—, —O—C(=O)—O—, —NR$^1$—C(=O)—, or —C(=O)—NR$^1$—.

$R^1$ represents a hydrogen atom or an alkyl group having a carbon number of 1-6.

Examples of alkyl groups having a carbon number of 1-6 that may be represented by $R^1$ include a methyl group, an ethyl group, an n-propyl group, an isopropyl group, an n-butyl group, a sec-butyl group, a t-butyl group, an n-pentyl group, and an n-hexyl group.

$R^1$ is preferably a hydrogen atom or an alkyl group having a carbon number of 1-4.

Moreover, among the above examples, it is preferable that $Y^1$ and $Y^2$ are each, independently of one another, a chemical single bond, —O—, —O—C(=O)—, or —C(=O)—O—.

$G^1$ represents an optionally substituted divalent chain aliphatic group having a carbon number of 1-20.

Herein, the phrase "optionally substituted" means "unsubstituted or having one or more substituents" (note that this phrase has the same meaning hereinafter).

Examples of the divalent chain aliphatic group having a carbon number of 1-20 include alkylene groups having a carbon number of 1-20 such as a methylene group, an ethylene group, a trimethylene group, a propylene group, a tetramethylene group, a pentamethylene group, a hexamethylene group, an octamethylene group, and a decamethylene group (—(CH$_2$)$_{10}$—); and alkenylene groups having a carbon number of 2-20 such as a vinylene group, a 1-methylvinylene group, a propenylene group, a 1-butenylene group, a 2-butenylene group, a 1-pentenylene group, and a 2-pentenylene group.

Examples of possible substituents for the divalent chain aliphatic group $G^1$ include halogen atoms such as a fluorine atom, a chlorine atom, a bromine atom, and an iodine atom; and alkoxy groups having a carbon number of 1-6 such as a methoxy group, an ethoxy group, an n-propoxy group, an isopropoxy group, an n-butoxy group, a sec-butoxy group, a t-butoxy group, an n-pentyloxy group, and an n-hexyloxy group. Among these substituents, a fluorine atom, a methoxy group, and an ethoxy group are preferable.

The chain aliphatic group may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—. However, the chain aliphatic group is not interrupted by two or more adjacent —O— or —S—. In the same way as $R^1$, $R^2$ represents a hydrogen atom or an alkyl group having a carbon number of 1-6, and is preferably a hydrogen atom or a methyl group.

The group interrupting the chain aliphatic group is preferably —O—, —O—C(=O)—, —C(=O)—O—, or —C(=O)—.

Specific examples of chain aliphatic groups interrupted by a group such as described above include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, and —CH$_2$—C(=O)—CH$_2$—.

Among the groups described above, $G^1$ is preferably an optionally substituted divalent chain aliphatic group having a carbon number of 1-12 (the aliphatic group may be interrupted by —O—, —O—C(=O)—, —C(=O)—O—, or —C(=O)—, but is not interrupted by two or more adjacent —O—), more preferably a divalent chain aliphatic group such as an alkylene group having a carbon number of 1-12 or an alkenylene group having a carbon number of 2-20, further preferably an alkylene group having a carbon number of 1-12, and particularly preferably a tetramethylene group (—(CH$_2$)$_4$—), a hexamethylene group (—(CH$_2$)$_6$—), an octamethylene group (—(CH$_2$)$_8$—), or a decamethylene group (—(CH$_2$)$_{10}$—).

$A^1$ and $A^2$ each represent, independently of one another, an optionally substituted divalent alicyclic hydrocarbon group having a carbon number of 3-12 or an optionally substituted divalent aromatic hydrocarbon group having a carbon number of 3-12.

Examples of the divalent alicyclic hydrocarbon group having a carbon number of 3-12 include cycloalkanediyl groups having a carbon number of 3-12 and divalent alicyclic fused ring groups having a carbon number of 7-12.

Examples of cycloalkanediyl groups having a carbon number of 3-12 include a cyclopropanediyl group; cyclobutanediyl groups such as a cyclobutane-1,2-diyl group and a cyclobutane-1,3-diyl group; cyclopentanediyl groups such as a cyclopentane-1,2-diyl group and a cyclopentane-1,3-diyl group; cyclohexanediyl groups such as a cyclohexane-1,2-diyl group, a cyclohexane-1,3-diyl group, and a cyclohexane-1,4-diyl group; cycloheptanediyl groups such as a cycloheptane-1,2-diyl group, a cycloheptane-1,3-diyl group, and a cycloheptane-1,4-diyl group; cyclooctanediyl groups such as a cyclooctane-1,2-diyl group, a cyclooctane-1,3-diyl group, a cyclooctane-1,4-diyl group, and a cyclooctane-1,5-diyl group; cyclodecanediyl groups such as a cyclodecane-1,2-diyl group, a cyclodecane-1,3-diyl group, a cyclodecane-1,4-diyl group, and a cyclodecane-1,5-diyl group; and cyclododecanediyl groups such as a cyclododecane-1,2-diyl group, a cyclododecane-1,3-diyl group, a cyclododecane-1,4-diyl group, and a cyclododecane-1,5-diyl group.

Examples of divalent alicyclic fused ring groups having a carbon number of 7-12 include decalindiyl groups such as a decalin-2,5-diyl group and a decalin-2,7-diyl group; adamantanediyl groups such as an adamantane-1,2-diyl group and an adamantane-1,3-diyl group; and bicyclo[2.2.1]heptanediyl groups such as a bicyclo[2.2.1]heptane-2,3-diyl group, a bicyclo[2.2.1]heptane-2,5-diyl group, and a bicyclo[2.2.1]heptane-2,6-diyl group.

These divalent alicyclic hydrocarbon groups may be optionally substituted at any position.

Examples of possible substituents include halogen atoms such as a fluorine atom and a chlorine atom; a cyano group; alkyl groups having a carbon number of 1-6 such as a methyl group, an ethyl group, and a propyl group; alkenyl groups having a carbon number of 2-6 such as a vinyl group and an allyl group; haloalkyl groups having a carbon number of 1-6 such as a trifluoromethyl group; substituted amino groups such as a dimethylamino group; alkoxy groups having a carbon number of 1-6 such as a methoxy group, an ethoxy group, and an isopropoxy group; a nitro group; aryl groups having a carbon number of 6-20 such as a phenyl group and a naphthyl group; —C(=O)—R$^6$; —C(=O)—OR$^6$; and —SO$_2$R$^6$. R$^6$ represents an alkyl group having a carbon number of 1-6 such as a methyl group or an ethyl group; or an aryl group having a carbon number of 6-14 such as a phenyl group.

Among the examples listed above, the optionally substituted divalent alicyclic hydrocarbon group having a carbon number of 3-12 is preferably an optionally substituted cycloalkanediyl group having a carbon number of 3-12, and is more preferably an optionally substituted cyclohexanediyl group.

The groups represented by formulae (A31) to (A34) shown below are preferable examples of the aforementioned cycloalkanediyl group having a carbon number of 3-12.

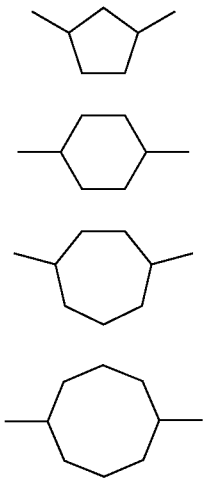

(A31)

(A32)

(A33)

(A34)

Cis and trans stereoisomers of the divalent alicyclic hydrocarbon group having a carbon number of 3-12 exist based on the difference in configuration of adjacent carbon atoms. For example, in the case of a cyclohexane-1,4-diyl group, a cis isomer (A32a) and a trans isomer (A32b) exist as shown below.

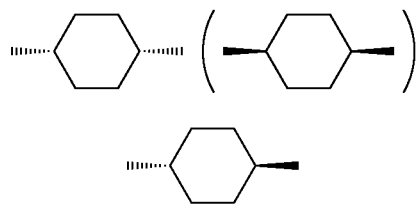

(A32a)

(A32b)

Herein, the cis isomer, the trans isomer, or a mixture of the cis and trans isomers may be present. However, in terms of favorable orientation, it is preferable that the trans isomer is present or the cis isomer is present, and more preferable that the trans isomer is present.

The divalent aromatic hydrocarbon group having a carbon number of 3-12 that may be represented by $A^1$ and $A^2$ may be a monocyclic group or a polycyclic group.

The following groups are specific preferable examples.

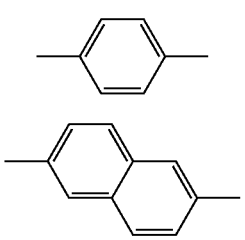

(A41)

(A42)

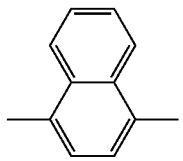

(A43)

The divalent aromatic hydrocarbon group having a carbon number of 3-12 that may be represented by $A^1$ and $A^2$ may be optionally substituted at any position.

Examples of possible substituents include a halogen atom, a cyano group, a hydroxyl group, an alkyl group having a carbon number of 1-6, an alkoxy group having a carbon number of 1-6, a nitro group, and a —C(=O)—OR$^7$ group. R$^7$ represents an alkyl group having a carbon number of 1-6. Among these substituents, a halogen atom, an alkyl group having a carbon number of 1-6, and an alkoxy group are preferable. The halogen atom is preferably a fluorine atom, the alkyl group having a carbon number of 1-6 is preferably a methyl group, an ethyl group, or a propyl group, and the alkoxy group is preferably a methoxy group or an ethoxy group.

Among the examples listed above, the optionally substituted divalent aromatic hydrocarbon group having a carbon number of 3-12 is preferably an optionally substituted phenylene group, and more preferably an optionally substituted group represented by formula (A41) shown above.

In formula (I), n represents 0 or 1.

Compound (I) used herein can be produced by a commonly known conventional method.

Compound (I) can typically be produced by freely combining reactions for forming an ether bond (—O—), a thioether bond (—S—), an ester bond (—C(=O)—O—, —O—C(=O)—), a carbonate bond (—O—C(=O)—O—), an amide bond (—C(=O)—NH—, —NH—C(=O)—), and the like in order to appropriately bond or modify a plurality of commonly known compounds having desired structures.

For example, ether bond formation can be carried out by any of the following methods.

(i) A compound represented by a formula D1-hal (hal represents a halogen atom and D1 represents any organic group (hal and D1 represent the same hereinafter)) and a compound represented by a formula D2-OMet (Met represents an alkali metal (normally sodium) and D2 represents any organic group (Met and D2 represent the same hereinafter)) are mixed and caused to undergo condensation (Williamson synthesis).

(ii) A compound represented by a formula D1-hal or a compound represented by a formula D1-J (J represents an epoxy group) and a compound represented by a formula D2-OH are mixed and caused to undergo condensation in the presence of a base such as sodium hydroxide or potassium hydroxide.

(iii) A compound represented by a formula D1-OFN (OFN represents a group having an unsaturated bond) and a compound represented by a formula D2-OMet are mixed and caused to undergo an addition reaction in the presence of a base such as sodium hydroxide or potassium hydroxide.

(iv) A compound represented by a formula D1-hal and a compound represented by a formula D2-OMet are mixed and caused to undergo condensation in the presence of copper or copper(I) chloride (Ullmann condensation).

Ester bond formation and amide bond formation can be carried out by any of the following methods.

(v) A compound represented by a formula D1-COOH and a compound represented by a formula D2-OH or D2-NH$_2$ are caused to undergo dehydration condensation in the presence of a dehydration condensing agent (for example, N,N-dicyclohexylcarbodiimide).

(vi) A halogenating agent is caused to act on a compound represented by a formula D1-COOH to obtain a compound represented by a formula D1-CO-hal that is then reacted with a compound represented by a formula D2-OH or D2-NH$_2$ in the presence of a base.

(vii) An acid anhydride is caused to act on a compound represented by a formula D1-COOH to obtain a mixed acid anhydride that is then reacted with a compound represented by a formula D2-OH or D2-NH$_2$.

(viii) A compound represented by a formula D1-COOH and a compound represented by a formula D2-OH or D2-NH$_2$ are caused to undergo dehydration condensation in the presence of an acid catalyst or a base catalyst.

In a more specific example, a compound represented by formula (I-1) shown below, which is a compound for which n in formula (I) is 1 and Y$^2$ in formula (I) is —O—C(=O)—, can be obtained as shown below.

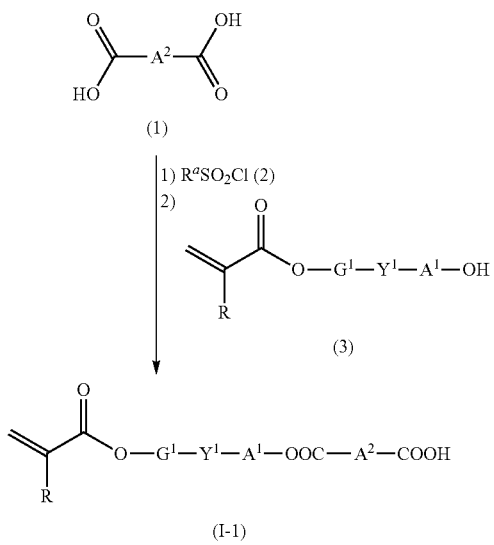

(In the above formulae, R, G$^1$, Y$^1$, A$^1$, and A$^2$ represent the same as previously described, and R$^a$ represents an alkyl group such as a methyl group or an ethyl group; or an optionally substituted aryl group such as a phenyl group or a p-methylphenyl group.)

In other words, a sulfonyl chloride represented by formula (2) is first reacted with a compound represented by formula (1) (compound (1)) in the presence of a base such as triethylamine or 4-(dimethylamino)pyridine.

Next, a compound represented by formula (3) (compound (3)) and a base such as triethylamine or 4-(dimethylamino)pyridine are added to and reacted with the resultant reaction mixture.

The amount of the sulfonyl chloride that is used is normally from 0.5 equivalents to 0.7 equivalents relative to 1 equivalent of compound (1).

The amount of compound (3) that is used is normally from 0.5 equivalents to 0.6 equivalents relative to 1 equivalent of compound (1).

The amount of the base that is used is normally from 0.5 equivalents to 0.7 equivalents relative to 1 equivalent of compound (1).

The reaction temperature is from 20° C. to 30° C. The reaction time is dependent on the scale of the reaction and so forth, but is of the order of a few minutes to several hours.

Examples of the solvent used in the above reaction include the same examples as described further below for an organic solvent. Among these solvents, ether solvents are preferable.

The amount of the solvent that is used can be set as appropriate in consideration of the types of compounds that are used, the scale of the reaction, and so forth without any specific limitations and is normally from 1 g to 50 g relative to 1 g of compound (1).

In the presently disclosed production method, compound (I) is reacted with a halogenating agent in the presence of a nitrogen atom-containing polar aprotic solvent.

Examples of the nitrogen atom-containing polar aprotic solvent include amide solvents such as N,N-dimethylformamide, N,N-dimethylacetamide, N,N-diethylformamide, N-methylpyrrolidone, 1,3-dimethyl-2-imidazolidinone, and hexamethylphosphoric triamide; nitrogen-containing heterocyclic compound solvents such as pyridine; and nitrile solvents such as acetonitrile. Among these solvents, an amide solvent is preferable, and at least one selected from the group consisting of N,N-dimethylformamide, N,N-dimethylacetamide, N-methylpyrrolidone, and 1,3-dimethyl-2-imidazolidinone is more preferable.

One nitrogen atom-containing polar aprotic solvent may be used individually, or two or more nitrogen atom-containing polar aprotic solvents may be used in combination.

The amount of the nitrogen atom-containing polar aprotic solvent that is used relative to compound (I) is at least 0.5 equivalents, and preferably at least 1.0 equivalents. If the amount of the nitrogen atom-containing polar aprotic solvent is too small, it is not possible to obtain the effect disclosed herein. Although no specific upper limit is set for the amount of the nitrogen atom-containing polar aprotic solvent, since the same effect is obtained even when the amount is large, the amount is normally no greater than 100 equivalents, and preferably no greater than 10 equivalents.

No specific restrictions are placed on the halogenating agent that is used in the presently disclosed production method, and any halogenating agent that can convert a carboxylic acid to a corresponding carboxylic acid halide can be used without any specific limitations. Specific examples of the halogenating agent include chlorinating agents such as thionyl chloride, oxalyl chloride, phosphoryl chloride, sulfuryl chloride, phosphorus trichloride, phosphorus pentachloride, and phosgene; brominating agents such as phosphorus tribromide; and iodizing agents such as iodine monochloride. Among these halogenating agents, chlorinating agents and brominating agents are preferable, and, from a viewpoint of ease of handling, thionyl chloride, oxalyl chloride, and sulfuryl chloride are more preferable, and thionyl chloride is particularly preferable.

One of such halogenating agents may be used individually, or two or more of such halogenating agents may be used in combination.

The amount of the halogenating agent that is used relative to compound (I) is from 1.1 equivalents to 3 equivalents, and preferably from 1.2 equivalents to 1.5 equivalents.

The reaction is preferably carried out in an organic solvent.

No specific limitations are placed on the organic solvent other than being an organic solvent that is inert with respect to the reaction. Examples of organic solvents that can be used include aromatic hydrocarbon solvents such as benzene, toluene, and xylene; hydrocarbon solvents such as hexane and heptane; cyclic hydrocarbon solvents such as cyclohexane and methylcyclohexane; chlorine-containing solvents such as chloroform, dichloromethane, 1,2-dichloroethane, chlorobenzene, and orthodichlorobenzene; ether solvents such as diethyl ether, tetrahydrofuran, 1,2-dimethoxyethane, 1,4-dioxane, 1,3-dioxolane, and cyclopentyl methyl ether; ester solvents such as ethyl acetate, propyl acetate, and methyl propionate; aliphatic hydrocarbon solvents such as n-pentane, n-hexane, and n-heptane; amide solvents such as N,N-dimethylformamide, N-methylpyrrolidone, and hexamethylphosphoric triamide; sulfur-containing solvents such as dimethyl sulfoxide and sulfolane; and mixed solvents of any two or more of the preceding organic solvents.

Among these organic solvents, aromatic hydrocarbon solvents such as benzene, toluene, and xylene; hydrocarbon solvents such as hexane and heptane; cyclic hydrocarbon solvents such as cyclohexane and methylcyclohexane; and chlorine-containing solvents such as chloroform, dichloromethane, 1,2-dichloroethane, chlorobenzene, and orthodichlorobenzene are preferable.

The amount of the organic solvent that is used can be set as appropriate in consideration of the scale of the reaction and so forth without any specific limitations and is normally from 1 g to 100 g relative to 1 g of compound (I).

The reaction temperature is in a temperature range from −10° C. to the boiling point of the organic solvent that is used.

The reaction time is dependent on the scale of the reaction, but is normally from 30 minutes to 10 hours.

Once the reaction is complete, post-reaction treatment operations that are normally used in organic synthetic chemistry may be carried out, and any commonly known means of separation or purification may be used as desired in order to isolate the target compound (II).

The structure of the target compound can for example be identified through measurement of an NMR spectrum, an IR spectrum, a mass spectrum, or the like, or through elemental analysis, or the like.

According to the presently disclosed production method, production of compound (III) as a by-product can be inhibited and the target compound (II) can be obtained with a yield of almost 100% and a high purity of normally at least 98%, and preferably at least 99.5%.

As described further below, even when the reaction mixture obtained upon completion of the reaction is, for example, stored for approximately 24 hours at normal temperature (20° C. to 30° C.), conversion of the target compound (II) to compound (III), leading to a decrease in the content of compound (II), does not occur.

2) Composition

The presently disclosed composition contains a compound represented by formula (II) shown below, either or both of a halogenating agent and a halogenating agent-derived product, and a nitrogen atom-containing polar aprotic solvent in an amount of at least 0.5 equivalents relative to the compound represented by formula (II).

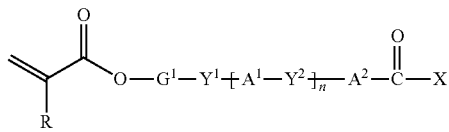

(II)

(In formula (II), R, X, $G^1$, $Y^1$, $Y^2$, $A^1$, $A^2$, and n represent the same as previously described.)

Examples of compound (II) and the halogenating agent include the same examples as provided in section 1) pertaining to the production method.

The term "halogenating agent-derived product" refers to a by-product of a reaction between a carboxylic acid and a halogenating agent. The halogenating agent-derived product may for example be a hydrogen halide such as hydrogen chloride or hydrogen bromide.

Examples of the nitrogen atom-containing polar aprotic solvent include the same examples as previously described. Among these solvents, an amide solvent is preferable, and at least one selected from the group consisting of N,N-dimethylformamide, N,N-dimethylacetamide, N-methylpyrrolidone, and 1,3-dimethyl-2-imidazolidinone is more preferable.

The content of the nitrogen atom-containing polar aprotic solvent relative to compound (II) is normally at least 0.5 equivalents, and preferably at least 1.0 equivalents. If the content of the nitrogen atom-containing polar aprotic solvent is too small, it is not possible to obtain a stabilization effect. Although no specific limitations are placed on the upper limit for the content of the nitrogen atom-containing polar aprotic solvent, since the same effect is obtained even when the content is high, the content is normally no greater than 100 equivalents, and preferably no greater than 10 equivalents.

The presently disclosed composition preferably further contains an organic solvent.

Examples of the organic solvent include the same examples as provided for the organic solvent used in the reaction in the production method described in section 1).

The amount of the organic solvent that is used is not specifically limited, but is preferably from 1 g to 100 g relative to 1 g of compound (II).

Compound (II) is converted to compound (III) over time if either or both of a halogenating agent and a halogenating agent-derived product are present therewith. In order to prevent this conversion, methods for completely removing the halogenating agent and/or halogenating agent-derived product have been considered. However, in the presently disclosed composition, compound (II) is stabilized by the nitrogen atom-containing polar aprotic solvent such that even if a halogenating agent or the like is present in the composition, the composition can be stored for a long time without compound (II) being converted to compound (III) and without a resulting decrease in the content of compound (II) in the composition.

The presently disclosed composition may for example be a reaction mixture that is obtained by reacting compound (I) with a halogenating agent in an organic solvent as desired in the presence of at least 0.5 equivalents, relative to compound (I), of a nitrogen atom-containing polar aprotic solvent, or may be a product obtained by removing a low boiling point substance from this reaction mixture.

Even when the reaction mixture is, for example, stored as-produced for approximately 24 hours at normal temperature after the target compound (II) has been obtained with a yield of almost 100%, conversion of compound (II) to compound (III) does not occur. Consequently, it is not necessary to subject the reaction mixture to post-reaction treatment or a next process soon after the reaction, and the reaction mixture can be subjected to the next process as-produced even after having been stored for a long time.

3) Stabilization Method

The presently disclosed stabilization method for compound (II) includes providing a nitrogen atom-containing polar aprotic solvent, in an amount of at least 0.5 equivalents relative to compound (II), in an organic solvent solution containing compound (II) and either or both of a halogenating agent and a halogenating agent-derived product.

Compound (II), the halogenating agent and/or halogenating agent-derived product, the nitrogen atom-containing polar aprotic solvent, the organic solvent, and the respective amounts thereof may for example be the same as described in sections 1) and 2).

The amount of the organic solvent that is used is not specifically limited, but is preferably from 1 g to 100 g relative to 1 g of compound (II).

According to the presently disclosed stabilization method, even when the organic solvent solution containing compound (II) and the halogenating agent and/or halogenating agent-derived product is stored for a long period, such as approximately 24 hours, conversion of compound (II) to a halogenated by-product (compound (III)) is inhibited and, as a result, a decrease in the content of compound (II) in the organic solvent solution is inhibited.

4) Compound (II)

As explained above in sections 1) and 2), the presently disclosed compound is a compound represented by formula (II) (compound (II))

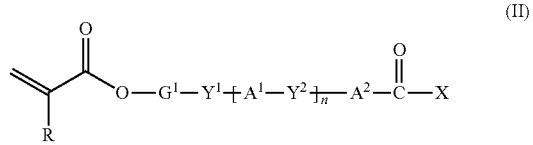

(II)

where, in formula (II):

R represents a hydrogen atom or a methyl group;

$Y^1$ and $Y^2$ each represent, independently of one another, a chemical single bond, —O—, —S—, —O—C(=O)—, —C(=O)—O—, —O—C(=O)—O—, —NR$^1$—C(=O)—, or —C(=O)—NR$^1$—, where R$^1$ represents a hydrogen atom or an alkyl group having a carbon number of 1-6;

$G^1$ represents an optionally substituted divalent chain aliphatic group having a carbon number of 1-20 that may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—, but is not interrupted by two or more adjacent —O— or —S—, where R$^2$ represents a hydrogen atom or an alkyl group having a carbon number of 1-6;

$A^1$ and $A^2$ each represent, independently of one another, an optionally substituted divalent aromatic hydrocarbon group having a carbon number of 3-12 or an optionally substituted divalent alicyclic hydrocarbon group having a carbon number of 3-12;

X represents a halogen atom; and n represents 0 or 1.

Specific examples of R, $Y^1$, $Y^2$, $G^1$, $A^1$, $A^2$, X, and n include the same examples as listed in the section pertaining to the presently disclosed production method.

In the presently disclosed compound, R$^1$ is preferably a hydrogen atom or an alkyl group having a carbon number of 1-4.

$Y^1$ and $Y^2$ are preferably each, independently of one another, a chemical single bond, —O—, —O—C(=O)—, or —C(=O)—O—.

$G^1$ is preferably an optionally substituted divalent chain aliphatic group having a carbon number of 1-12 (the aliphatic group may be interrupted by —O—, —O—C(=O)—, —C(=O)—O—, or —C(=O)—, but is not interrupted by two or more adjacent —O—), more preferably a divalent chain aliphatic group such as an alkylene group having a carbon number of 1-12 or an alkenylene group having a carbon number of 2-20, further preferably an alkylene group having a carbon number of 1-12, and particularly preferably a tetramethylene group (—(CH$_2$)$_4$—), a hexamethylene group (—(CH$_2$)$_6$—), an octamethylene group (—(CH$_2$)$_8$—), or a decamethylene group (—(CH$_2$)$_{10}$—).

The optionally substituted divalent alicyclic hydrocarbon group having a carbon number of 3-12 that may be represented by A$^1$ and A$^2$ is preferably an optionally substituted cycloalkanediyl group having a carbon number of 3-12, more preferably an optionally substituted group represented by any of the previously shown formulae (A31) to (A34), further preferably an optionally substituted group represented by formula (A32), and particularly preferably a group represented by formula (A32b).

The divalent aromatic hydrocarbon group having a carbon number of 3-12 that may be represented by A$^1$ and A$^2$ is preferably a group represented by any one of the previously shown formulae (A41) to (A43), and is more preferably a group represented by formula (A41).

For the presently disclosed compound (II), n in formula (II) is preferably 1 and X in formula (II) is preferably a fluorine atom, a chlorine atom, or a bromine atom, and more preferably a chlorine atom.

Compound (II) described above is useful as a production intermediate of a polymerizable compound that can be used to prepare an optical film capable of uniform polarized light conversion over a wide wavelength range.

EXAMPLES

The following provides a more detailed explanation of the present disclosure through examples. However, the present disclosure is not in any way limited by the following examples.

(Synthesis Example 1): Synthesis of Compound (Ia)

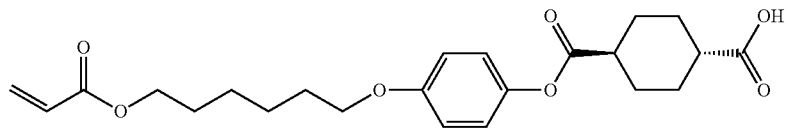 [SMILES: C=CC(=O)OCCCCCCOc1ccc(OC(=O)[C@H]2CC[C@H](C(=O)O)CC2)cc1]

Compound (Ia)

A three-neck reaction vessel equipped with a thermometer was charged with 90 g (0.52 mol) of trans-1,4-cyclohexanedicarboxylic acid and 800 mL of tetrahydrofuran (THF) in a nitrogen gas stream. Next, 33 g (0.29 mol) of methanesulfonyl chloride was added into the reaction vessel, the reaction vessel was immersed in a water bath, and the internal temperature of the reaction liquid was set to 20° C. Thereafter, 31.7 g (0.31 mol) of triethylamine was dripped into the reaction vessel over a period of 30 minutes while maintaining the internal temperature of the reaction liquid at from 20° C. to 30° C. After completion of this dripping, all contents of the reaction vessel were stirred for 2 hours at 25° C.

Next, 3.2 g (26.2 mmol) of 4-(dimethylamino)pyridine and 69 g (0.26 mol) of 4-(6-acryloyloxy-hex-1-yloxy)phenol (produced by DKSH) were added to the resultant reaction liquid, the reaction vessel was once again immersed in the water bath, and the internal temperature of the reaction liquid was set to 15° C. Thereafter, 31.7 g (0.31 mmol) of triethylamine was dripped into the reaction vessel over a period of 30 minutes while maintaining the internal temperature of the reaction liquid at from 20° C. to 30° C. After completion of this dripping, all contents of the reaction vessel were stirred for 2 hours at 25° C. Once the reaction was complete, 4,000 mL of distilled water and 500 mL of saturated saline were added to the reaction liquid, and two extractions were performed with 1,000 mL of ethyl acetate. The resultant organic layers were collected together, were dried using anhydrous sodium sulfate, and the sodium sulfate was then separated by filtration. Solvent was removed from the filtrate by evaporation using a rotary evaporator. Thereafter, the resultant residue was purified by silica gel column chromatography (THF:toluene=1:9 (volume ratio)) to yield 70.6 g of compound (Ia) as a white solid. The yield was 65%.

The structure of the target product was identified by $^1$H-NMR.

$^1$H-NMR (500 MHz, DMSO-$d_6$, TMS, δ ppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Example 1

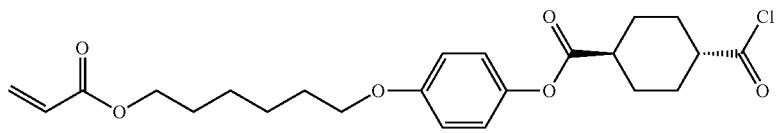 [SMILES: C=CC(=O)OCCCCCCOc1ccc(OC(=O)[C@H]2CC[C@H](C(=O)Cl)CC2)cc1]

Compound (IIa)

A three-neck reaction vessel equipped with a thermometer was charged with 30 g (71.7 mmol) of compound (Ia) obtained in Synthesis Example 1, 300 g of toluene, and 5.5 g (75.2 mmol) of N,N-dimethylformamide in a nitrogen gas stream, and all contents of the reaction vessel were cooled to 10° C. or lower. Next, 9.14 g (76.8 mmol) of thionyl chloride was dripped into the reaction vessel while maintaining the reaction temperature at 10° C. or lower. After completion of this dripping, the reaction temperature was returned to 25° C. and all contents of the reaction vessel were stirred for 4 hours at the same temperature. In Table 1 shown further below, this method is referred to as reaction method I.

Once the reaction was complete, the following reaction was carried out in order to convert the target compound (IIa) to compound 2 shown below and to convert a by-product compound (IIIa) shown below to compound 3 so that the content of compound (IIIa) in the reaction mixture could be calculated.

Specifically, once the reaction was complete, 1.0 g of the reaction liquid was sampled and was stirred with 0.1 g of methanol for 5 minutes. Next, 1.0 g of water and 0.2 g of ethyl acetate were added to the reaction mixture and a liquid separation operation was carried out. Thereafter, the organic layer was analyzed by high performance liquid chromatography (HPLC) and the contents of compound 2 and compound 3 were measured. The results showed that the content of compound 2, which in other words is the content of compound (IIa), was 98.81 weight %, and the content of compound (IIIa), which in other words is the content of compound 3, was 1.19 weight %.

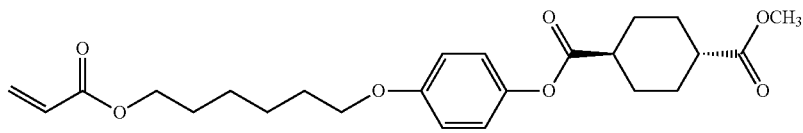

Compound 2

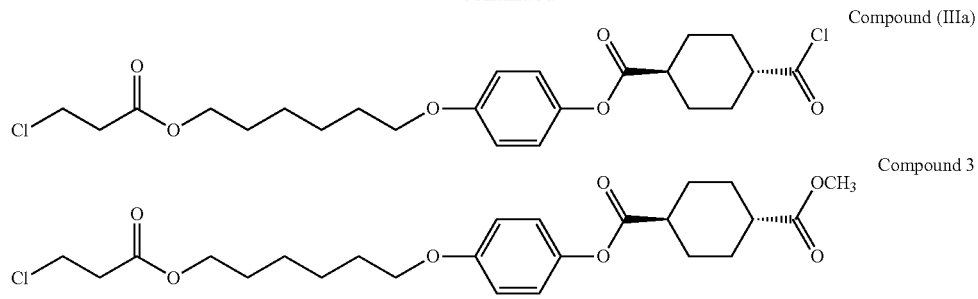

Compound (IIIa)

Compound 3

Example 2

The same operations as in Example 1 were carried out with the exception that 5.5 g (75.2 mmol) of N,N-dimethylformamide in Example 1 was changed to 7.9 g (108.1 mmol) of N,N-dimethylformamide. The results are summarized in Table 1 further below.

Example 3

The same operations as in Example 1 were carried out with the exception that 5.5 g (75.2 mmol) of N,N-dimethylformamide in Example 1 was changed to 10.5 g (143.7 mmol) of N,N-dimethylformamide. The results are summarized in Table 1 further below.

Example 4

The same operations as in Example 1 were carried out with the exception that 5.5 g (75.2 mmol) of N,N-dimethylformamide in Example 1 was changed to 26.2 g (358.5 mmol) of N,N-dimethylformamide. The results are summarized in Table 1 further below.

Example 5

The same operations as in Example 1 were carried out with the exception that 5.5 g (75.2 mmol) of N,N-dimethylformamide in Example 1 was changed to 300 mg (4.1 mmol) of N,N-dimethylformamide and 6.55 g (75.2 mmol) of N,N-dimethylacetamide. The results are summarized in Table 1 further below.

Example 6

The same operations as in Example 1 were carried out with the exception that 5.5 g (75.2 mmol) of N,N-dimethylformamide in Example 1 was changed to 7.45 g (75.2 mmol) of N-methylpyrrolidone and 300 mg (4.1 mmol) of N,N-dimethylformamide. The results are summarized in Table 1 further below.

Example 7

The same operations as in Example 1 were carried out with the exception that 5.5 g (75.2 mmol) of N,N-dimethylformamide in Example 1 was changed to 8.58 g (75.2 mmol) of 1,3-dimethyl-2-imidazolidinone and 300 mg (4.1 mmol) of N,N-dimethylformamide. The results are summarized in Table 1 further below.

Example 8

A three-neck reaction vessel equipped with a thermometer was charged with 30 g (71.7 mmol) of compound (Ia) synthesized in Synthesis Example 1, 300 g of toluene, and 5.5 g (75.2 mmol) of N,N-dimethylformamide in a nitrogen gas stream, and all contents of the reaction vessel were cooled to 10° C. or lower. Next, 9.14 g (76.8 mmol) of thionyl chloride was dripped into the reaction vessel while maintaining the reaction temperature at 10° C. or lower. After completion of this dripping, the reaction liquid was returned to 25° C. and was stirred for 1 hour at the same temperature. Once the reaction was complete, the reaction liquid was concentrated using an evaporator until the amount thereof had halved. Thereafter, toluene was added in an amount equivalent to the amount that had been removed and the reaction liquid was concentrated again using the evaporator until the amount thereof had halved. This operation was repeated three times and the resultant toluene solution was stored for 24 hours at 23° C. In Table 1 shown further below, this method is referred to as reaction method II.

Once the reaction was complete, the same operations as in Example 1 were performed in order to convert the target compound (IIa) to compound 2 and to convert the by-product compound (IIIa) to compound 3 so that the contents of compound (IIa) and compound (IIIa) in the reaction mixture could be calculated. The results are summarized in Table 1 further below.

Example 9

The same operations as in Example 8 were carried out with the exception that 5.5 g (75.2 mmol) of N,N-dimethylformamide in Example 8 was changed to 7.9 g (108.1 mmol) of N,N-dimethylformamide. The results are summarized in Table 1 further below.

Example 10

The same operations as in Example 8 were carried out with the exception that 5.5 g (75.2 mmol) of N,N-dimethylformamide in Example 8 was changed to 10.5 g (143.7 mmol) of N,N-dimethylformamide. The results are summarized in Table 1 further below.

Example 11

The same operations as in Example 8 were carried out with the exception that 5.5 g (75.2 mmol) of N,N-dimethylformamide in Example 8 was changed to 26.2 g (358.5 mmol) of N,N-dimethylformamide. The results are summarized in Table 1 further below.

Example 12

The same operations as in Example 8 were carried out with the exception that 5.5 g (75.2 mmol) of N,N-dimethylformamide in Example 8 was changed to 6.55 g (75.2 mmol) of N,N-dimethylacetamide and 300 mg (4.1 mmol) of N,N-dimethylformamide. The results are summarized in Table 1 further below.

Example 13

The same operations as in Example 8 were carried out with the exception that 5.5 g (75.2 mmol) of N,N-dimethylformamide in Example 8 was changed to 7.45 g (75.2 mmol) of N-methylpyrrolidone and 300 mg (4.1 mmol) of N,N-dimethylformamide. The results are summarized in Table 1 further below.

Example 14

The same operations as in Example 8 were carried out with the exception that 5.5 g (75.2 mmol) of N,N-dimethylformamide in Example 8 was changed to 8.58 g (75.2 mmol) of 1,3-dimethyl-2-imidazolidinone and 300 mg (4.1 mmol) of N,N-dimethylformamide. The results are summarized in Table 1 further below.

Comparative Example 1

The same operations as in Example 1 were carried out with the exception that 5.5 g (75.2 mmol) of N,N-dimethylformamide in Example 1 was changed to 300 mg (4.1 mmol) of N,N-dimethylformamide. The results are summarized in Table 1 further below.

Comparative Example 2

The same operations as in Example 1 were carried out with the exception that 5.5 g (75.2 mmol) of N,N-dimethylformamide in Example 1 was changed to 1.05 g (14.4 mmol) of N,N-dimethylformamide. The results are summarized in Table 1 further below.

Comparative Example 3

The same operations as in Example 1 were carried out with the exception that 5.5 g (75.2 mmol) of N,N-dimethylformamide in Example 1 was changed to 6.47 g (75.2 mmol) of γ-butyrolactone and 300 mg (4.1 mmol) of N,N-dimethylformamide. The results are summarized in Table 1 further below.

Comparative Example 4

The same operations as in Example 8 were carried out with the exception that 5.5 g (75.2 mmol) of N,N-dimethylformamide in Example 8 was changed to 300 mg (4.1 mmol) of N,N-dimethylformamide. The results are summarized in Table 1 further below.

Comparative Example 5

The same operations as in Example 8 were carried out with the exception that 5.5 g (75.2 mmol) of N,N-dimethylformamide in Example 8 was changed to 1.05 g (14.4 mmol) of N,N-dimethylformamide. The results are summarized in Table 1 further below.

Comparative Example 6

The same operations as in Example 8 were carried out with the exception that 5.5 g (75.2 mmol) of N,N-dimethylformamide in Example 8 was changed to 6.47 g (75.2 mmol) of γ-butyrolactone and 300 mg (4.1 mmol) of N,N-dimethylformamide. The results are summarized in Table 1 further below.

Example 15

The same operations as in Example 1 were carried out with the exception that 300 g of toluene in Example 1 was changed to 300 g of chloroform (produced by Tokuyama Corporation, amylene stabilized product). The results are summarized in Table 2 further below.

Example 16

The same operations as in Example 15 were carried out with the exception that 5.5 g (75.2 mmol) of N,N-dimethylformamide in Example 15 was changed to 10.5 g (143.7 mmol) of N,N-dimethylformamide. The results are summarized in Table 2 further below.

Example 17

The same operations as in Example 15 were carried out with the exception that 5.5 g (75.2 mmol) of N,N-dimethylformamide in Example 15 was changed to 26.2 g (358.5 mmol) of N,N-dimethylformamide. The results are summarized in Table 2 further below.

Example 18

A three-neck reaction vessel equipped with a thermometer was charged with 30 g (71.7 mmol) of compound (Ia) synthesized in Synthesis Example 1, 300 g of chloroform (produced by Tokuyama Corporation, amylene stabilized product), and 5.5 g (75.2 mmol) of N,N-dimethylformamide in a nitrogen gas stream, and all contents of the reaction vessel were cooled to 10° C. or lower. Next, 9.14 g (76.8 mmol) of thionyl chloride was dripped into the reaction vessel while maintaining the reaction temperature at 10° C. or lower. After completion of this dripping, the reaction liquid was returned to 25° C. and was stirred for 1 hour at the same temperature. Once the reaction was complete, concentrating was performed using an evaporator and, after 225 g of chloroform had been removed, dilution was performed by newly adding 75 g of chloroform (produced by Tokuyama Corporation, amylene stabilized product). The resultant chloroform solution was stored for 24 hours at 23° C. In Table 2 shown further below, this method is referred to as reaction method III.

Example 19

The same operations as in Example 18 were carried out with the exception that 5.5 g (75.2 mmol) of N,N-dimethylformamide in Example 18 was changed to 10.5 g (143.7 mmol) of N,N-dimethylformamide. The results are summarized in Table 2 further below.

Example 20

The same operations as in Example 18 were carried out with the exception that 5.5 g (75.2 mmol) of N,N-dimethylformamide in Example 18 was changed to 26.2 g (358.5 mmol) of N,N-dimethylformamide. The results are summarized in Table 2 further below.

Comparative Example 7

The same operations as in Example 15 were carried out with the exception that 5.5 g (75.2 mmol) of N,N-dimethylformamide in Example 15 was changed to 1.05 g (14.4 mmol) of N,N-dimethylformamide. The results are summarized in Table 2 further below.

Comparative Example 8

The same operations as in Example 18 were carried out with the exception that 5.5 g (75.2 mmol) of N,N-dimethylformamide in Example 18 was changed to 1.05 g (14.4 mmol) of N,N-dimethylformamide. The results are summarized in Table 2 further below.

C: N-Methylpyrrolidone
D: 1,3-Dimethyl-2-imidazolidinone
E: γ-Butyrolactone

From Tables 1 and 2, it can be seen that in Examples 1-20 in which at least 0.5 equivalents of a nitrogen atom-containing polar aprotic solvent was added, production of compound 3, and thus also production of compound (IIIa), was significantly inhibited.

Moreover, the results for Examples 5, 6, 7, 12, 13, and 14 confirm that when N,N-dimethylformamide was used in combination with N,N-dimethylacetamide, N-methylpyrrolidone, or 1,3-Dimethyl-2-imidazolidinone, a similar or better inhibitive effect was obtained compared to when N,N-dimethylformamide was used individually.

TABLE 1

| | Polar aprotic solvent | | | | | | | |
|---|---|---|---|---|---|---|---|---|
| | First type of solvent | | | Second type of solvent | | | | |
| | Type | Amount (g) | Amount (equivalents) | Type | Amount (g) | Amount (equivalents) | Reaction method | Compound 2 (%) | Compound 3 (%) |
| Example 1 | A | 5.50 | 1.05 | — | — | — | I | 98.81 | 1.19 |
| Example 2 | A | 7.90 | 1.50 | — | — | — | I | 99.62 | 0.38 |
| Example 3 | A | 10.50 | 2.00 | — | — | — | I | 99.77 | 0.23 |
| Example 4 | A | 26.20 | 5.00 | — | — | — | I | 99.89 | 0.11 |
| Example 5 | A | 0.30 | 0.06 | B | 6.55 | 1.05 | I | 100.00 | 0.00 |
| Example 6 | A | 0.30 | 0.06 | C | 7.45 | 1.05 | I | 99.65 | 0.36 |
| Example 7 | A | 0.30 | 0.06 | D | 8.58 | 1.05 | I | 99.75 | 0.25 |
| Example 8 | A | 5.50 | 1.05 | — | — | — | II | 99.54 | 0.46 |
| Example 9 | A | 7.90 | 1.50 | — | — | — | II | 99.84 | 0.16 |
| Example 10 | A | 10.50 | 2.00 | — | — | — | II | 99.85 | 0.15 |
| Example 11 | A | 26.20 | 5.00 | — | — | — | II | 99.91 | 0.09 |
| Example 12 | A | 0.30 | 0.06 | B | 6.55 | 1.05 | II | 100.00 | 0.00 |
| Example 13 | A | 0.30 | 0.06 | C | 7.45 | 1.05 | II | 99.90 | 0.10 |
| Example 14 | A | 0.30 | 0.06 | D | 8.58 | 1.05 | II | 99.94 | 0.06 |
| Comparative Example 1 | A | 0.30 | 0.06 | — | — | — | I | 81.77 | 18.23 |
| Comparative Example 2 | A | 1.05 | 0.20 | — | — | — | I | 94.13 | 5.87 |
| Comparative Example 3 | A | 0.30 | 0.06 | E | 6.47 | 1.05 | I | 81.90 | 18.10 |
| Comparative Example 4 | A | 0.30 | 0.06 | — | — | — | II | 88.92 | 11.08 |
| Comparative Example 5 | A | 1.05 | 0.20 | — | — | — | II | 97.12 | 2.88 |
| Comparative Example 6 | A | 0.30 | 0.06 | E | 6.47 | 1.05 | II | 89.05 | 10.95 |

TABLE 2

| | Polar aprotic solvent | | | | | | | |
|---|---|---|---|---|---|---|---|---|
| | First type of solvent | | | Second type of solvent | | | | |
| | Type | Amount (g) | Amount (equivalents) | Type | Amount (g) | Amount (equivalents) | Reaction method | Compound 2 (%) | Compound 3 (%) |
| Example 15 | A | 5.50 | 1.05 | — | — | — | I | 99.07 | 0.93 |
| Example 16 | A | 10.50 | 2.00 | — | — | — | I | 99.81 | 0.19 |
| Example 17 | A | 26.20 | 5.00 | — | — | — | I | 99.88 | 0.12 |
| Example 18 | A | 5.50 | 1.05 | — | — | — | III | 99.77 | 0.23 |
| Example 19 | A | 10.50 | 2.00 | — | — | — | III | 99.89 | 0.11 |
| Example 20 | A | 26.20 | 5.00 | — | — | — | III | 99.95 | 0.05 |
| Comparative Example 7 | A | 1.05 | 0.20 | — | — | — | I | 93.98 | 6.02 |
| Comparative Example 8 | A | 1.05 | 0.20 | — | — | — | III | 97.99 | 2.01 |

A to E in Tables 1 and 2 represented the following.
A: N,N-Dimethylformamide
B: N,N-Dimethylacetamide In contrast, in Comparative Examples 1-8 in which less than 0.5 equivalents of a nitrogen atom-containing polar aprotic solvent was used, the content of compound 3, and thus also the content of compound (IIIa), was high compared to the aforementioned examples. Moreover, even when at least 0.5 equivalents of γ-butyrolactone, which is a polar aprotic solvent, was used and the halogenating agent, which may act as a cause of a side reaction, was removed, it was not possible to obtain favorable results (Comparative Examples 3 and 6).

(Example 21): Measurement of Change Over Time in Synthesis of Compound (IIa)

A three-neck reaction vessel equipped with a thermometer was charged with 30 g (71.7 mmol) of compound (Ia) synthesized in Synthesis Example 1, 300 g of toluene, and 5.5 g (75.2 mmol; 1.05 equivalents) of N,N-dimethylformamide in a nitrogen gas stream, and cooling was performed to 10° C. or lower. Next, 9.14 g (76.8 mmol) of thionyl chloride was dripped into the reaction vessel while maintaining the reaction temperature at 10° C. or lower. After completion of this dripping, the reaction liquid was returned to 25° C. and was stirred for 24 hours at the same temperature.

A 1.0 g sample was taken from the reaction liquid after 1 hour, 2 hours, 3 hours, 4 hours, 6 hours, 12 hours, 18 hours, and 24 hours. Each of the samples was stirred with 0.1 g of methanol, and after compound (IIa) contained in the sample had been converted to compound 2 and compound (IIIa) contained in the sample had been converted to compound 3, 1.0 g of water and 0.2 g of ethyl acetate were added and a liquid separation operation was carried out. Thereafter, the organic layer was analyzed by high performance liquid chromatography (HPLC) and the contents of compound 2 and compound 3 were measured in order to obtain the purity and track the change in purity. The results are summarized in Table 3 further below and in the graph in FIGURE.

In FIGURE, the vertical axis indicates the content (%) of compound 2 and the horizontal axis indicates time (hr).

Example 22

The same operations as in Example 21 were carried out with the exception that 5.5 g (75.2 mmol) of N,N-dimethylformamide in Example 21 was changed to 7.9 g (108.1 mmol; 1.5 equivalents) of N,N-dimethylformamide. The results are summarized in Table 3 further below and in the graph in FIGURE.

Example 23

The same operations as in Example 21 were carried out with the exception that 5.5 g (75.2 mmol) of N,N-dimethylformamide in Example 21 was changed to 10.5 g (143.7 mmol; 2.0 equivalents) of N,N-dimethylformamide. The results are summarized in Table 3 further below and in the graph in FIGURE.

Example 24

The same operations as in Example 21 were carried out with the exception that 5.5 g (75.2 mmol) of N,N-dimethylformamide in Example 21 was changed to 26.2 g (358.5 mmol; 5.0 equivalents) of N,N-dimethylformamide. The results are summarized in Table 3 further below and in the graph in FIGURE.

Comparative Example 9

The same operations as in Example 21 were carried out with the exception that 5.5 g (75.2 mmol) of N,N-dimethylformamide in Example 21 was changed to 300 mg (4.1 mmol; 0.06 equivalents) of N,N-dimethylformamide. The results are summarized in Table 3 further below and in the graph in FIGURE.

Comparative Example 10

The same operations as in Example 21 were carried out with the exception that 5.5 g (75.2 mmol) of N,N-dimethylformamide in Example 21 was changed to 1.05 g (14.4 mmol; 0.2 equivalents) of N,N-dimethylformamide. The results are summarized in Table 3 further below and in the graph in FIGURE.

Comparative Example 11

The same operations as in Example 21 were carried out with the exception that 5.5 g (75.2 mmol) of N,N-dimethylformamide in Example 21 was changed to 6.47 g (75.2 mmol; 1.05 equivalents) of γ-butyrolactone and 300 mg (4.1 mmol; 0.06 equivalents) of N,N-dimethylformamide. The results are summarized in Table 3 further below and in the graph in FIGURE.

TABLE 3

|  | After 1 hour | | After 2 hours | | After 3 hours | | After 4 hours | |
| --- | --- | --- | --- | --- | --- | --- | --- | --- |
|  | Compound 2 (%) | Compound 3 (%) | Compound 2 (%) | Compound 3 (%) | Compound 2 (%) | Compound 3 (%) | Compound 2 (%) | Compound 3 (%) |
| Example 21 | 100.00 | 0.00 | 100.00 | 0.00 | 99.24 | 0.76 | 98.81 | 1.19 |
| Example 22 | 100.00 | 0.00 | 100.00 | 0.00 | 100.00 | 0.00 | 99.62 | 0.38 |
| Example 23 | 100.00 | 0.00 | 100.00 | 0.00 | 100.00 | 0.00 | 99.77 | 0.23 |
| Example 24 | 100.00 | 0.00 | 100.00 | 0.00 | 100.00 | 0.00 | 99.89 | 0.11 |
| Comparative Example 9 | 99.32 | 0.68 | 95.45 | 4.55 | 88.68 | 11.32 | 81.19 | 18.81 |
| Comparative Example 10 | 100.00 | 0.00 | 98.61 | 1.39 | 96.13 | 3.87 | 94.13 | 5.87 |
| Comparative Example 11 | 99.30 | 0.70 | 95.48 | 4.52 | 85.55 | 14.46 | 81.90 | 18.10 |

|  | After 6 hours | | After 12 hours | | After 18 hours | | After 24 hours | |
| --- | --- | --- | --- | --- | --- | --- | --- | --- |
|  | Compound 2 (%) | Compound 3 (%) | Compound 2 (%) | Compound 3 (%) | Compound 2 (%) | Compound 3 (%) | Compound 2 (%) | Compound 3 (%) |
| Example 21 | 97.25 | 2.75 | 96.78 | 3.22 | 95.65 | 4.35 | 95.00 | 5.00 |
| Example 22 | 99.03 | 0.97 | 98.84 | 1.16 | 98.29 | 1.71 | 97.85 | 2.15 |

TABLE 3-continued

| | | | | | | | | |
|---|---|---|---|---|---|---|---|---|
| Example 23 | 99.35 | 0.65 | 99.18 | 0.82 | 99.00 | 1.00 | 98.51 | 1.49 |
| Example 24 | 99.67 | 0.33 | 99.59 | 0.41 | 99.33 | 0.67 | 99.00 | 1.00 |
| Comparative Example 9 | 72.45 | 27.55 | 62.78 | 37.22 | 58.37 | 41.63 | 55.47 | 44.53 |
| Comparative Example 10 | 92.88 | 7.12 | 90.39 | 9.61 | 87.67 | 12.33 | 85.69 | 14.31 |
| Comparative Example 11 | 75.83 | 24.17 | 63.15 | 36.85 | 57.88 | 42.12 | 57.48 | 42.52 |

From Table 3 and the graph in FIGURE, it can be seen that in Examples 21-24 in which from 0.5 equivalents to 5 equivalents of a nitrogen atom-containing polar aprotic solvent was used relative to compound (IIa) (equivalent amount to compound (Ia) since the reaction yield was almost 100%), after completion of the reaction, production of compound 3 (i.e., compound (IIIa)) was inhibited even over time (1-24 hours). For example, the purity of compound 2 (i.e., compound (IIa)) was at least 99% even after 3 hours had passed and was still at least 95% even after 24 hours had passed.

In contrast, it can be seen that in Comparative Examples 9 and 10 in which the amount of nitrogen atom-containing polar aprotic solvent that was used was less than 0.5 equivalents, compound (IIa) was converted to compound (IIIa), leading to a progressive decrease in the content of compound (IIa). Moreover, it can be seen that despite γ-butyrolactone, which is a "non-nitrogen atom-containing polar aprotic solvent", being used in an amount of 1.05 equivalents relative to compound (IIa) in Comparative Example 11, the effect described above was not obtained.

The invention claimed is:

1. A production method for a compound of formula (II)

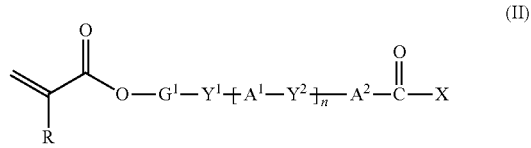

(II)

comprising
reacting a compound of formula (I)

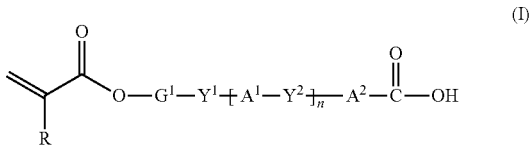

(I)

with a halogenating agent in the presence of at least 0.5 equivalents, relative to the compound of formula (I), of a nitrogen atom-containing polar aprotic solvent, wherein
in formula (I):
R is a hydrogen atom or a methyl group;
$Y^1$ is a chemical single bond, —O—, —S—, —O—C(=O)—, —C(=O)—O—, —O—C(=O)—O—, —NR$^1$—C(=O)—, or —C(=O)—NR$^1$—, where $R^1$ is a hydrogen atom or an alkyl group having a carbon number of 1-6;
$Y^2$ is —O—, —S—, —O—C(=O)—, —C(=O)—O—, —O—C(=O)—O—, —NR$^1$—C(=O)—, or —C(=O)—NR$^1$—, where $R^1$ is a hydrogen atom or an alkyl group having a carbon number of 1-6;

$G^1$ is an optionally substituted divalent chain aliphatic group having a carbon number of 1-20 that may be interrupted by —O—, —S—, —O—C(=O)—, —C(=O)—O—, —O—C(=O)—O—, —NR$^2$—C(=O)—, —C(=O)—NR$^2$—, —NR$^2$—, or —C(=O)—, but is not interrupted by two or more adjacent —O— or —S—, where $R^2$ is a hydrogen atom or an alkyl group having a carbon number of 1-6;
$A^1$ and $A^2$ each are, independently of one another, an optionally substituted divalent aromatic hydrocarbon group having a carbon number of 3-12 or an optionally substituted divalent alicyclic hydrocarbon group having a carbon number of 3-12; and
n is 1, and
in formula (II), R, $G^1$, $Y^1$, $Y^2$, $A^1$, $A^2$, and n is the same as above, and X is a halogen atom.

2. The production method of claim 1, wherein the halogenating agent is a chlorinating agent or a brominating agent.

3. The production method of claim 1, wherein the compound of formula (I) is a compound for which, in formula (I), $Y^1$ is a chemical single bond, —O—, —O—C(=O)—, or —C(=O)—O—, $Y^2$ is —O—, —O—C(=O)—, or —C(=O)—O—, and $G^1$ is an optionally substituted divalent chain aliphatic group having a carbon number of 1-20.

4. The production method of claim 1, wherein the compound of formula (I) is a compound for which, in formula (I), $A^1$ and $A^2$ are each, independently of one another, an optionally substituted phenylene group or an optionally substituted cyclohexylene group.

5. The production method of claim 1, wherein the nitrogen atom-containing polar aprotic solvent is an amide solvent.

6. The production method of claim 1, wherein the nitrogen atom-containing polar aprotic solvent is at least one selected from the group consisting of N,N-dimethylformamide, N,N-dimethylacetamide, N-methylpyrrolidone, and 1,3-dimethyl-2-imidazolidinone.

7. The production method of claim 1, further comprising after the reacting, concentrating a reaction liquid and removing either or both of unreacted halogenating agent and a halogenating agent-derived product.

8. A composition comprising:
a compound of formula (II);

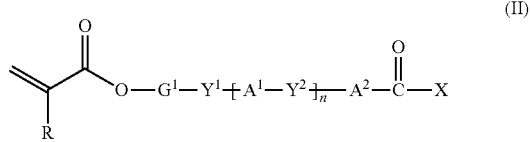

(II)

either or both of a halogenating agent and a halogenating agent-derived product; and a nitrogen atom-containing polar aprotic solvent in an amount of at least 0.5 equivalents relative to the compound of formula (II), wherein in formula (II):

R is a hydrogen atom or a methyl group;

$Y^1$ is a chemical single bond, —O—, —S—, —O—C(=O)—, —C(=O)—O—, —O—C(=O)—O—, —$NR^1$—C(=O)—, or —C(=O)—$NR^1$—, where $R^1$ is a hydrogen atom or an alkyl group having a carbon number of 1-6;

$Y^2$ is —O—, —S—, —O—C(=O)—, —C(=O)—O—, —O—C(=O)—O—, —$NR^1$—C(=O)—, or —C(=O)—$NR^1$—, where $R^1$ is a hydrogen atom or an alkyl group having a carbon number of 1-6;

$G^1$ is an optionally substituted divalent chain aliphatic group having a carbon number of 1-20 that may be interrupted by —O—, —S—, —O—C(=O)—, —C(=O)—O—, —O—C(=O)—O—, —$NR^2$—C(=O)—, —C(=O)—$NR^2$—, —$NR^2$—, or —C(=O)—, but is not interrupted by two or more adjacent —O— or —S—, where $R^2$ is a hydrogen atom or an alkyl group having a carbon number of 1-6;

$A^1$ and $A^2$ each are, independently of one another, an optionally substituted divalent aromatic hydrocarbon group having a carbon number of 3-12 or an optionally substituted divalent alicyclic hydrocarbon group having a carbon number of 3-12;

X is a halogen atom; and n is 1.

9. The composition of claim 8, further comprising an organic solvent other than the nitrogen atom-containing polar aprotic solvent.

10. The composition of claim 8, wherein the nitrogen atom-containing polar aprotic solvent is an amide solvent.

11. The composition of claim 8, wherein the nitrogen atom-containing polar aprotic solvent is at least one selected from the group consisting of N,N-dimethylformamide, N,N-dimethylacetamide, N-methylpyrrolidone, and 1,3-dimethyl-2-imidazolidinone.

12. A stabilization method for a compound of formula (II)

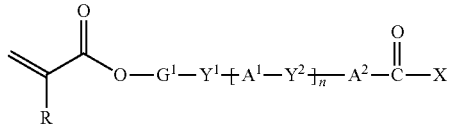

(II)

comprising providing a nitrogen atom-containing polar aprotic solvent, in an amount of at least 0.5 equivalents relative to the compound of formula (II), in an organic solvent solution containing the compound of formula (II) and either or both of a halogenating agent and a halogenating agent-derived product, wherein in formula (II):

R is a hydrogen atom or a methyl group;

$Y^1$ is a chemical single bond, —O—, —S—, —O—C(=O)—, —C(=O)—O—, —O—C(=O)—O—, —$NR^1$—C(=O)—, or —C(=O)—$NR^1$—, where $R^1$ is a hydrogen atom or an alkyl group having a carbon number of 1-6;

$Y^2$ is —O—, —S—, —O—C(=O)—, —C(=O)—O—, —O—C(=O)—O—, —$NR^1$—C(=O)—, or —C(=O)—$NR^1$—, where $R^1$ is a hydrogen atom or an alkyl group having a carbon number of 1-6;

$G^1$ is an optionally substituted divalent chain aliphatic group having a carbon number of 1-20 that may be interrupted by —O—, —S—, —O—C(=O)—, —C(=O)—O—, —O—C(=O)—O—, —$NR^2$—C(=O)—, —C(=O)—$NR^2$—, —$NR^2$—, or —C(=O)—, but is not interrupted by two or more adjacent —O— or —S—, where $R^2$ is a hydrogen atom or an alkyl group having a carbon number of 1-6;

$A^1$ and $A^2$ each are, independently of one another, an optionally substituted divalent aromatic hydrocarbon group having a carbon number of 3-12 or an optionally substituted divalent alicyclic hydrocarbon group having a carbon number of 3-12;

X is a halogen atom; and n is 1.

13. A compound of formula (II)

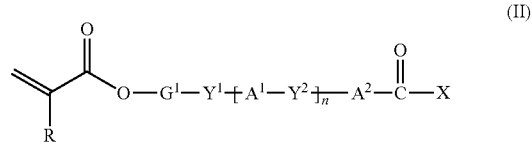

(II)

where, in formula (II):

R is a hydrogen atom or a methyl group;

$Y^1$ is a chemical single bond, —O—, —S—, —O—C(=O)—, —C(=O)—O—, —O—C(=O)—O—, —$NR^1$—C(=O)—, or —C(=O)—$NR^1$—, where $R^1$ is a hydrogen atom or an alkyl group having a carbon number of 1-6;

$Y^2$ is —O—, —S—, —O—C(=O)—, —C(=O)—O—, —O—C(=O)—O—, —$NR^1$—C(=O)—, or —C(=O)—$NR^1$—, where $R^1$ is a hydrogen atom or an alkyl group having a carbon number of 1-6;

$G^1$ is an optionally substituted divalent chain aliphatic group having a carbon number of 1-20 that may be interrupted by —O—, —S—, —O—C(=O)—, —C(=O)—O—, —O—C(=O)—O—, —$NR^2$—C(=O)—, —C(=O)—$NR^2$—, —$NR^2$—, or —C(=O)—, but is not interrupted by two or more adjacent —O— or —S—, where $R^2$ is a hydrogen atom or an alkyl group having a carbon number of 1-6;

$A^1$ is an optionally substituted divalent aromatic hydrocarbon group having a carbon number of 3-12 or an optionally substituted divalent alicyclic hyrdocarbon group having a carbon number of 3-12;

$A^2$ is an optionally substituted divalent alicyclic hydrocarbon group having a carbon number of 3-12, an unsubstituted divalent aromatic hydrocarbon group which has a carbon number of 3-12, or a divalent aromatic hydrocarbon group which has a carbon number of 3-12 and is substituted by at least one substituent selected from the group consisting of a halogen atom, a cyano group, a hydroxyl group, an alkyl group having a carbon number of 1-6, a nitro group, and a —C(=O)-$OR^7$ group, where $R^7$ is an alkyl group having a carbon number of 1-6;

X is a halogen atom; and n is 1.

14. The compound of claim 13, wherein in formula (II), X is a fluorine atom, a chlorine atom, or a bromine atom.

* * * * *